US006224873B1

(12) United States Patent
Jones

(10) Patent No.: US 6,224,873 B1
(45) Date of Patent: May 1, 2001

(54) REGULATION OF APPETITE, BODY WEIGHT AND ATHLETIC FUNCTION WITH MATERIALS DERIVED FROM CITRUS VARIETIES

(75) Inventor: Dennis Jones, Shelbume, VT (US)

(73) Assignee: Zhishin, LLC, South Burlington, VT (US)

(*) Notice: Subject to any disclaimer, the term of this patent is extended or adjusted under 35 U.S.C. 154(b) by 0 days.

(21) Appl. No.: 09/142,197

(22) PCT Filed: Sep. 30, 1996

(86) PCT No.: PCT/US96/16213

§ 371 Date: Aug. 31, 1998

§ 102(e) Date: Aug. 31, 1998

(87) PCT Pub. No.: WO98/14200

PCT Pub. Date: Apr. 9, 1998

(51) Int. Cl.$^7$ .......................... A61K 35/78; A61K 31/24; A61K 31/16; A61K 31/135; A61K 47/00
(52) U.S. Cl. ...................... 424/195.1; 514/534; 514/535; 514/626; 514/653; 514/789; 514/909
(58) Field of Search .................. 424/195.1; 514/626, 514/909, 534, 535, 653, 789

(56) References Cited

FOREIGN PATENT DOCUMENTS

| 5164 | 6/1967 | (FR) . |  |
| 91/00730 | 1/1991 | (WO) | A61K/31/52 |

OTHER PUBLICATIONS

Font Quer, P., (1982), "Plantes Medicinales; el Dioscorides renovado", pp. 95–97, 435438, Editorial Labor S.A., Madrid.
Malchow–Moller, A., et al., 1980, Effekten af Helsingor––pillen i behandlingen af adipositas. En kontrolleret klinisk undersogelse. Ugeskr. Laeger., 142, 1496–1499.
Roed, P., et al., 1980, Helsingor–slankepiller. En kontrolleret klinisk undersogelse i almen praksis. Ugeskr. Laeger., 142, 1491–1495.
Beeman et al., *J. Econ. Entomol*, 71(6):859–861, 1978.
Davenport et al., *Physiol. Entomol*, 9(3):269–274, 1984.
Hosoda et al., *Yakugaku Zasshi*, 111(3)188–192, 1984.
Jia et al., Bullentin on Human Medical College, 8:267–271, 1983.
Kinoshita et al., Shoyakugaku Zasshi, 33(3):146–149, 1979.
Namba et al., Shoyakugaku Zasshi, 39(1):52–62, 1985.
Zhao et al., Chinese Medical Journal, 102(2):91–93, 1989.
Dialog: Chapman & Hall Chemical Database 1989/Nov., "2–Methylamino–1–phenyl–1–propanol".
Dialog: The Merck Index Online (SM) 1984, 1985, 1992, "Norpseudoephadrine".
Dialog: The Merck Index Online (SM) 1984, 1985, 1992, "Ephedrine".
"Ephedra" from *Encyclopedia of Herbs*, C. Kowalchik and W.H. Hylton, eds. (Rodale Press: Emmaus, Penn.), 1987, p. 184.

Dulloo et al., *Nutrition*, 5(1):7–9, Jan./Feb., 1989.
Gerard, J., *The Herbal or General History of Plants*, pp. 1116–1117, published 1633, reissued 1975, Dover Publications, Inc., New York.
Jonkerko, K. et al., *Aliment. Pharmacol. Therap.*, 5:413–418, 1991.
Quaade, F. et al., *Ugeskr Læger*, 154/18:1258–1263, Apr. 1992.
Tyler, V.E., *The Honest Herbal*, pp. 151–152, George F. Stickley Company, Philadelphia, PA.
Colker, C. et al., *Current Therapeutic Research*, 60(3):145–153, Mar., 1999.
Jones, Dennis, All Natural Muscular Development, Feb. 1998, 109–176.
Halman, D.S., *Muscular Development*, pp. 122–125.
Hedrei, P. et al., application for Student Research Day, Dec. 3, 1997, Abstract.
Arner, P., "Adenosine, prostaglandins and phosphodiesterase as targets for obesity", *International Journal of Obesity* (1993) 17 (Suppl. 1), S57–S59.
Astrup, A., "Thermogenesis in human brown adipose tissue and skeletal muscle induced by sympathomimetic stimulation", *Acta Endocrino Logica* (1986) 112 (Suppl. 278), pp. 2–32.
Astrup, A., et al., "Enhanced thermogenic responsiveness during chronic ephedrine treatment in man", *The American Journal Clinical Nutrition* (1985) 42: 83–94.
Astrup, A., et al., "The Effect of Chronic Ephedrine Treatment on Substrate Utilization, the Sympathoadrenal Activity, and Energy Expenditure During Glucose–Induced Thermogenesis in Man", *Metabolism* (1986) 35:260–265.
Astrup, A., et al., "Thermogenic, Metabolic, and Cardiovascular Effects of a Sympathomimetic Agent, Ephedrine", *Current Therapeutic Research* (1990) 48, No. 6, pp. 1087–1100.

(List continued on next page.)

*Primary Examiner*—Kevin E. Weddington
(74) *Attorney, Agent, or Firm*—Darby & Darby

(57) ABSTRACT

Materials derived from Citrus plants can be administered orally to humans for the purpose of producing or maintaining weight loss as well as for improving the person's physical performance and increasing the person's lean muscle mass. The Citrus materials include those portions of the plant that are normally considered waste or inedible, such as the leaves, peel, and immature, unripe fruit. The materials contain at least one of the alkaloids from the group consisting of synephrine, hordenine, octopamine, tyramine and N-methyltyramine (1). Two species, *Citrus aurantium* and *Citrus reticulata*, are particularly useful. The materials can be administered in their natural form or as extracts, and can be administered in various ways including capsules and tablets. The Citrus materials may also be used as a tea. For weight loss and weight control, the materials can be administered concurrently with caloric restriction or in the absence of caloric restriction. The materials may also be administered for the purpose of increasing muscle mass concurrently with a high protein diet as well as with an exercise program.

12 Claims, 1 Drawing Sheet

OTHER PUBLICATIONS

Astrup, A., et al., "Caffeine: a double–blind, placebo–controlled study of its thermogenic, metabolic, and cardiovascular effects in healthy volunteers", *The American Journal of Clinical Nutrition* (1990) 51:759–67.

Astrup, A., et al., "The effect and safety of an ephedrine/caffeine compound compared to ephedrine, caffeine and placebo in obese subjects in an energy restricted diet. A double blind trial", *International Journal of Obesity* (1992) 16:269–277.

Astrup, A., et al., "The Effect of Ephedrine/Caffeine Mixture on Energy Expenditure and Body Composition in Obese Women", *Metabolism* (1992) 41: No. 7, pp. 686–688.

Astrup, A., et al., "Ephedrine and Weight Loss", *International Journal of Obesity* (1992) 16:715.

Astrup, A., et al., "Pharmacology of thermogenic drugs", *The American Journal of Clinical Nutrition* (1992) 55:246S–8S.

Astrup, A., et al., "Thermogenic, metabolic, and cardiovascular responses to ephedrine and caffeine in man", *International Journal of Obesity* (1993) 17 (Suppl. 1), pp. S41–S43.

Bown, D., *Encyclopedia of Herbs & Their Uses* (1995), pp. 108–109, 123.

Breum, L. et al., "Comparison of an ephedrine/caffeine combination and dexfenfluramine in the treatment of obesity. A double–blind multi–centre trial in general practice", *International Journal of Obesity* (1994) 18(2):99–103.

Buemann, B., et al., "The effect of ephedrine plus caffeine on plasma lipids and lipoproteins during a 4.2 MJ/day diet", *International Journal of Obesity* (1994) 18:329–332.

Court, J.M., "Effect of ephedrine in ketotic hypoglycaemia", *Archives of Disease in Childhood* (1974) 49: 63–65.

Daly, P.A., et al., "Ephedrine, caffeine and aspirin: safety and efficacy for treatment of human obesity", *International Journal of Obesity* (1993) 17 (Suppl. 1), pp. S73–S78.

Dulloo, A.G., et al., "The Thermogenic Properties of Ephedrine/Methylxanthine Mixtures: Human Studies", *International Journal of Obesity* (1986) 10:467–481.

Dulloo, A.G., et al., "Aspirin as a promoter of ephedrine–induced thermogenesis: potential use in the treatment of obesity", *The American Journal of Clinical Nutrition* (1987) 45:564–9.

Dulloo, A.G., et al., "Peripheral mechanisms of thermogenesis induced by ephedrine and caffeine in brown adipose tissue", *International Journal of Obesity* (1991) 15:317–326.

Dulloo, A.G., et al., "Ephedrine, xanthines and prostaglandin–inhibitors: actions and interactions in the stimulation of thermogenesis", *International of Journal of Obesity* (1993) 17 (Suppl. 1) pp. S35–S40.

Facts and Comparisons, A Wolters Kluwer Company, *Drug Facts and Comparisons* (1995 edition), pp. 962–993.

Gahart, B.L., RN, "Ephedrine Sulfate", *Intravenous Medications—a handbook for nurses and other allied health personnel* (1958) $4^{th}$ Edition, pp. 200–201.

Geissler, C.A., "Effects of weight loss, ephedrine and aspirin on energy expenditure in obese women", *International Journal of Obesity* (1993) 17 (Suppl. 1), pp. S45–S48.

Gerard, J., *The Herball, or General Historie of Plantes* (1597), 2 pages.

Govoni, L.E., Ph.D., RN, et al., "Ephedrine/Ephedrine Sulfate", *Drugs and Nursing Implications* (1985) $5^{th}$ Edition, pp. 496–499.

Grieve, M., "Ephedra", "Lemon", "Lime–Fruit" and "Sweet Orange", *A Modern Herbal—The Medicinal, Culinary, Cosmetic and Economic Properties, Cultivation and Folklore of Herbs, Grasses, Fungi, Shrubs and Trees With All Their Modern Scientific Uses* (1992), Revised Edition 1973, pp. 286, 474–476, 485, 601–602.

Hopkins, D.F.C., et al., "Effective Treatment of Insulin–Induced Edema Using Ephedrine", *Diabetes Care* (1993) 16, No. 7, pp. 1026–1028.

Huang, K.C., "Antishock Herbs", "Stomachic and 'Wind'–Dispelling Herbs" and "Other Stomachics and 'Wind'–Dispelling Agents", *The Pharmacology of Chinese Herbs* (1993), pp. 107–108, 173, 177.

Jones, D. et al., "Use of Herbs Containing Natural Source Ephedrine Alkaloids in Weight Loss Programmes", *International Journal of Obesity* (1993), 17 (Suppl. 1), p. S81.

Kaats, G.R., et al., "Effects of a Multiple Herbal Formulation on Body Composition, Blood Chemistry, Vital Signs, and Self–Reported Energy Levels & Appetite Control", *International Journal of Obesity* (1994) 18 (Suppl. 2), pp. 145.

Carr, A., et al., "Ephedra", *Rodale's Illustrated Encyclopedia of Herbs*, (1987) p. 184.

Krieger, D.R., et al., "Ephedrine, Caffeine and Aspirin Promote Weight Loss in Obese Subjects", *Trans. Assoc. Am. Phys.* (1990) 103:307–12.

Landsberg, M.D., et al., "Sympathoadrenal activity and obesity: physiological rationale for the use of adrenergic thermogenic drugs", *International Journal of Obesity* (1993) 17 (Suppl. 1), pp. S29–S34.

Lewis, W.H., et al., "Antiarrhythmic Drugs", "Plants Used to Relieve Toothache", "Phylogenetic Group 8 Myrtales" and "Antidiarrheal Agents", *Medical Botany—Plants Affecting Man's Health* (1977), pp. 189–190, 250–251, 254–255, 287.

Lowe, F.C., MD, et al., "Placebo–Controlled Study of Oral Terbutaline and Pseudoephedrine in Management of Prostaglandin E1–Induced Prolonged Erections", *Urology* (1993) 42, No. 1, pp. 51–54.

Malchow–Moller, A., et al., "Ephedrine as an anorectic: the story of the 'Elsinore pill'", *International Journal of Obesity* (1981) 5:183–187.

Weatherall, D.J., et al., "The Autonomic Nervous System", *Oxford Textbook of Medicine* (1983), vol. 2, Section 13–Index, pp. 21.22–21.23.

Molnar, D., "Effects of ephedrine and aminophylline on resting energy expenditure in obese adolescents", *International Journal of Obesity* (1993) 17 (Suppl. 1), S49–S52.

Hieble, J.P., et al., "Pharmacology of the Sympathetic Nervous System", *Principles of Pharmacology—Basic Concepts & Clinical Applications* (1995), pp. 122–144.

Nielsen, B., et al., "Effect of physical training on thermogenic responses to cold and ephedrine in obesity", *International Journal of Obesity* (1993) 17: 383–390.

Pasquali, R., et al., "A Controlled Trial Using Ephedrine in the Treatment of Obesity", *International Journal of Obesity* (1985) 9: 93–98.

Pasquali, R., et al., "Does Ephedrine Promote Weight Loss in Low–Energy–Adapted Obese Women?", *International Journal of Obesity* (1987) 11:163–168.

Pasquali, R., et al., "Thermogenic Agents in the Treatment of Human Obesity Preliminary Results", *International Journal of Obesity* (1987) 11 (Suppl. 3), pp. 23–26.

Pasquali, R., et al., "Effects of chronic administration of ephedrine during very–low–calorie diets on energy expenditure, protein metabolism and hormone levels in obese subjects", *Clinical Science* (1992) 82, pp. 85–92.

Pasquali, R., et al., "Clinical aspects of ephedrine in the treatment of obesity", *International Journal of Obesity* (1993) 17 (Suppl. 1), pp. S65–S68.

Reid, D.P., *Chinese Herbal Medicine* (1993), pp. 50, 8 and 126–127.

Reynolds, J.E.F., et al., "Ephedrine", *Martindale—The Extra Pharmacopoeia* (1982), 28$^{th}$ Edition, pp. 10–12, 671, 678–679.

Stokholm, K.H., et al., "Lowering of Serum Total $T_3$ During a Conventional Slimming Regine", *International Journal of Obesity* (1983) 7:195–199.

Streeten, D.H.P., "The Role of Posture in Idiopathic Oedema", *SA Mediese Tydskrif* (1975), pp. 462–464.

Stuart, M., "Bitter Orange" and "Ephedra", *The Encyclopedia of Herbs and Herbalism* (1979), pp. 175, 185.

Toubro, S., et al., "Safety and efficacy of long–term treatment with ephedrine, caffeine and an ephedrine/caffeine mixture", *International Journal of Obesity* (1993) 17 (Suppl. 1), pp. S69–S72.

Vallerand, A.L., "Effects of ephedrine/xanthines on thermogenesis and cold tolerance", *International Journal of Obesity* (1993) 17 (Suppl. 1), pp. S53–S56.

Wheaton, T.A., et al., "The Distribution of Tyramine, N–Methyltyramine, Hordenine, Octopamine, and Synephrine in Higher Plants", *Lloydia* (1970) 33 (No. 2), pp. 244,–254.

"Aurantii fructus immaturi", *Herbal Drugs and Phytopharmaceuticals* (1994), pp. 93–95.

Yang, Y.T., et al., "Multiple actions of β–adrenergic agonists on skeletal muscle and adipose tissue", *Biochem. J.* (1989) 261:1–10.

Ming, O., "Fructus Aurantii Immaturus", *Chinese–English Manual of Common–Used in Traditional Chinese Medicine* (1989), pp. 348–349.

REGULATION OF APPETITE, BODY WEIGHT AND ATHLETIC FUNCTION WITH MATERIALS DERIVED FROM CITRUS VARIETIES

TECHNICAL FIELD

The present invention relates to the use of materials derived from Citrus plants in inducing weight loss, improving physical performance and increasing muscle mass.

REFERENCES TO BACKGROUND ART

Arner, P., 1993, Adenosine, prostaglandins and phosphodiesterase as targets for obesity pharmacotherapy. Int. J. Obesity, 17, S57–S60.

Astrup, A., 1986, Thermogenesis in human brown adipose tissue and skeletal muscle induced by sympathicomimetic stimulation. Acta Endocrinol. Suppl., 278, 1–32.

Astrup, A., Lundsgaard, C., Madsen, J. and Christensen, N. J., 1985, Enhanced thermogenic responsiveness during chronic ephedrine treatment in man. Am. J. Clin. Nutr., 42, 83–94.

Astrup, A., Madsen, J., Hoist, J.J. and Christensen, N. J., 1986, The effect of chronic ephedrine treatment on substrate utilization, the sympathoadrenal activity, and energy expenditure during glucose-induced thermogenesis in man. Metabolism, 35, 260–265.

Astrup, A., Toubro, S., Cannon, S., Hein, P. and Madsen, J., 1990a, Thermogenic, metabolic and cardiovascular effects of a sympathicomimetic agent, ephedrine. Curr. Ther. Res., 48, 1087–1100.

Astrup, A., Toubro, S., Cannon, S., Hein, P. Breum, L. and Madsen, J., 1990b, Caffeine: a double-blind, placebo-controlled study of its thermogenic, metabolic and cardiovascular effects in healthy volunteers. Am. J. Clin. Nutr., 51, 759–767.

Astrup, A., Breum, L., Toubro, S., Hein, P. and Quaade, F., 1992a, The effect and safety of an ephedrine/caffeine compound compared to ephedrine, caffeine and placebo in obese subjects on an energy restricted diet. A double blind trial. Int. J. Obesity, 16, 169–277.

Astrup, A., Buemann, B., Christensen, N. J., Toubro, S., Thorbek, G., Victor, O. J. and Quaade, F., 1992b, The effect of ephedrine/caffeine mixture on energy expenditure and body composition in obese women. Metabolism, 41, 686–688.

Astrup, A., Breum, L., Toubro, S., Hein, P. and Quaade, F., 1992c, Ephedrine and weight loss. Int. J. Obesity, 16, 715.

Astrup, A., Toubro, S., Christensen, N. J. and Quaade, F., 1992d, Pharmacology of thermogenic drugs. Am. J. Clin. Nutr., 55, 246S–248S.

Astrup, A. and Toubro, S., 1993, Thermogenic, metabolic, and cardiovascular responses to ephedrine and caffeine in man. Int. J. Obesity, 17, S41–S44.

Bown, D., 1995, The Encyclopedia of Herbs & Their Uses. Dorling Kindersly, London.

Breum, L., Pedersen, J. K., Ahlstrom, F. and Frimodt-Moller, J., 1994, Comparison of an ephedrine/caffeine combination and dexfenfluramine in the treatment of obesity. A double-blind multi-center trial in general practice. Int. J. Obesity, 18, 99–103.

Buemann, B., Marckmann, P., Christensen, N. J. and Astrup, A., 1994, The effect of ephedrine plus caffeine on plasma lipids and lipoproteins during a 4.2 MJ/day diet. Int. J. Obesity, 18, 329–332.

Court, J. M., Dunlop, M. E. and Boulton, T. J., 1974, Effect of ephedrine in ketotic hypoglycaemia. Arch. Dis. Child., 49, 63–65.

Daly, P., Krieger, D., Dulloo, A., Young, J. and Landsberg, L., 1993, Ephedrine, caffeine and aspirin: safety and efficacy for treatment of human obesity. Int. J. Obesity, 17, S73–S78.

Drug Facts and Comparisons, 1995, Facts and Comparisons, St. Louis.

Dulloo, A. G. and Miller, D. S., 1986, The thermogenic properties of ephedrine/methylxanthine mixtures: human studies. Int. J. Obes., 10, 467–481.

Dulloo, A. G. and Miller, D. S., 1987, Aspirin as a promoter of ephedrine-induced thermogenesis: potential use in the treatment of obesity. Am. J. Clin. Nutr., 45, 564–569.

Dulloo, A. G. and Miller, D. S., 1989, Ephedrine, caffeine and aspirin: "over-the-counter" drugs that interact to stimulate thermogenesis in the obese. Nutrition 5, 7–9.

Dulloo, A. G., Seydoux, J. and Girardier, L., 1991, Peripheral mechanisms of thermogenesis induced by ephedrine and caffeine in brown adipose tissue. Int. J. Obes., 15, 317–326.

Dulloo, A. G., 1993, Ephedrine, xanthines and prostaglandin inhibitors: actions and interactions in the stimulation of thermogenesis. Int. J. Obesity, 17, S35–S40.

Font Quer, P., (1982), "Plantes Medicinales; el Dioscorides renovado". Editorial Labor S. A., Madrid.

Gahart, B. L., 1985, Intravenous medications; a Handbook for Nurses and other allied health professionals. 4th Edition, The C. V. Mosby Company, 200–201.

Geissler, C., 1993, Effects of weight loss, ephedrine and aspirin on energy expenditure in obese women. Int. J. Obesity, 17, S45–S48.

Gerard, J., 1597, The Herball or Generall Historie of Plantes, John Norton, London. Second Edition enlarged and amended by Thomas Johnson, 1633, and reprinted 1636 [Note: translation of Dodoens' Stirpium Historiae Pemptades Sex, Antwerp, 1583].

Govoni, L. E. and Hayes, J. E., 1985, Drugs and Nursing Implications. Appleton-Century-Crofts, Norwalk.

Grieve, M., 1992, A Modern Herbal. Dorset Press, New York.

Hopkins, D. F., Cotton, S. J. and Williams, G., 1993, Effective treatment of insulin-induced edema using ephedrine. Diabetes Care, 16, 1026–1028.

Huang, K. C., 1993. The Pharmacology of Chinese Herbs, 173. CRC Press, Boca Raton.

Jonderko, K. and Kucio, C., 1991, Effect of anti-obesity drugs promoting energy expenditure, yohimbine and ephedrine, on gastric emptying in obese patients. Aliment. Pharmacol. Ther., 5, 413–418.

Jones, D. and Egger, T. E., 1993, Use of herbs containing natural source ephedrine alkaloids in weight loss programmes. Int. J. Obes., 17, S81.

Kaats, G. R. and Adelman, J. A., 1994, Effects of a multiple herbal formulation on body composition, blood chemistry, vital signs, and self-reported energy levels & appetite control. Int. J. Obesity, 18 (Supp. 2), S145. Aso personal communication.

Kowalchik, C., and Hylton, W., 1987, Rodale's Illustrated Encyclopaedia of Herbs. Rodale Press, Emmaus, Penn.

Krieger, D. R., Daly, P. A., Dulloo, A. G., Ransil, B. J., Young, J. B. and Landsberg, L., 1990, Ephedrine, caffeine and aspirin promote weight loss in obese subjects. Trans. Assoc. Am. Physicians, 103, 307–312.

Landsberg, L. and Young, Y. B., 1993, Sympathoadrenal activity and obesity: physiological rationale for the use of adrenergic thermogenic drugs. Int. J. Obesity, 17, S29–S34.

Lewis, W. H. and Elvin-Lewis, M. P. F., 1977, Medical Botany. John Wiley & Sons, New York.

Li Shih-Chen, 1596, Ben Cao Kong Mu, Peking, China.

Lowe, F. C. and Jarow, J. P., 1993, Placebo-controlled study of oral terbutaline and pseudoephedrine in management of prostaglandin El-induced prolonged erections. Urology, 42, 51–54.

Malchow-Moller, A., Larsen, S., Hey, H., Stokholm, K. H., Juhl, E. and Quaade, F., 1980, Effekten af Helsingor-pillen i behandlingen af adipositas. En kontrolleret klinisk undersogelse. Ugeskr. Laeger., 142, 1496–1499.

Malchow-Moller, A., Larsen, S., Hey, H., Stokholm, K. H., Juhl, E. and Quaade, F., 1981, Ephedrine as an anorectic: the story of the 'Elsinore pill'. nt. J. Obes., 5, 183–187.

Matthews, W. B., 1983, The autonomic nervous system, in Oxford Textbook of Medicine, Ed. Weatherall, D. J., Ledingham, J. G. G. and Warrell, D. A., 21.23, Oxford University Press, Oxford, New York, Toronto.

Molnar, D., 1993, Effects of ephedrine and aminophylline on resting energy expenditure in obese adolescents. Int. J. Obesity, 17, S49–S52.

Moritz, O, 1953, Einfuhrung in die algemeine Pharmakognosie. 2nd Edition, Jena, 305–306.

Munson, P. L. (Ed.), 1995, principles of pharmacology; basic concepts and clinical applications. Chapman & Hall, New York.

Nielsen, B., Astrup, A., Samuelsen, P., Wengholt, H. and Christensen, N. J., 1993, Effect of physical training on thermogenic responses to cold and ephedrine in obesity. Int. J. Obesity, 17, 383–390.

Ou Ming, 1989, Chinese-English Manual of Common-Used in Traditional Chinese Medicine; Guangdong Science & Technology Publishing House and Joint Publishing (H. K.) Co., Ltd., Hong Kong.

Pasquali, R., Baraldi, G., Cesari, M. P., Melchionda, N., Zamboni, M., Stefanini, C. and Raitano, A., 1985, A controlled trial using ephedrine in the treatment of obesity. Int. J. Obes., 9, 93–98.

Pasquali. R., Cesari, M. P., Meichionda, N., Stefanini, C., Raitano, A. and Labo, G., 1987a, Does ephedrine promote weight loss in low-energy-adapted obese women? Int. J. Obes., 11, 163–168.

Pasquali. R., Cesari, M. P., Bestighi, L., Melchionda, N. and Balestra, V., 1987b, Thermogenic agents in the treatment of human obesity: preliminary results. Int. J. Obes., 11, Suppl. 3, 23–26.

Pasquali, R., Casimirri, F., Melchionda, N., Grossi, G., Bortoluzzi, L., Morselli Labate, A. M., Stefanini, C. and Raitano, A., 1992, Effects of chronic administration of ephedrine during very-low-calorie diets on energy expenditure, protein metabolism and hormone levels in obese subjects. Clin. Sci., 82, 85–92.

Pasquali, R. and Casimirri, F., 1993, Clinical aspects of ephedrine in the treatment of obesity. Int. J. Obesity, 17, S65–S68.

Quaade, F., Astrup, A., Breum, L., Toubro, S. and Hein, P., 1992, Effekten af en efedrin/koffein-kombination som understottelse af en affedningsdiaet. En randomiseret, placebokontrolleret, dobbeltblind undersogelse. Ugeskr. Laeger., 154, 1258–1263.

Reid, D. P., 1986, Chinese Herbal Medicine. Shambhala, Boston.

Reynolds, J. E. F., Ed., 1982, Martindale; the Extra Pharmacopoeia, 28th Edition. The Pharmaceutical Press, London.

Roed, P., Hansen, P. W., Bidstrup, B., Kaem, M., Helles, A. and Petersen, K. P., 1980, Helsingor-slankepiller. En kontrolleret klinisk undersogelse i almenpraksis. Ugeskr. Laeger., 142, 1491–1495.

Southon, I. W. and Buckingham, J., (Eds.), 1989, Dictionary of Alkaloids, 1st Edition, Main Work (Chapman & Hall). See also Dictionary of Organic Compounds, 1982, 5th Edition, Main Work (Chapman & Hall).

Stokholm, K. H. and Hansen, M. S., 1983, Lowering of serum total T3 during a conventional slimming regime. Int. J. Obes., 7, 195–199.

Streeten, D. H., 1975, The role of posture in idiopathic oedema. S. Afr. Med. J., 49, 462–464.

Stuart, M., 1979, The Encyclopaedia of Herbs and Herbalism. Orbis Publishing Limited, London.

Toubro, S., Astrup, A., Breum, L. and Quaade, F., 1993, Safety and efficacy of long-term treatment with ephedrine, caffeine and an ephedrine/caffeine mixture. Int. J. Obesity, 17, S69–S72.

Tyler, V. E., 1982, The Honest Herbal—A sensible guide to the use of herbs and related remedies. George F. Stickley, Philadelphia.

Vallerand, A., 1993, Effects of ephedrine/xanthines on thermogenesis and cold tolerance. Int. J. Obesity, 17, S53–S56.

Wheaton, T. A. and Stewart, I., 1970, The distribution of tyramine, N-methyltyramine, hordenine, octopamine and synephrine in higher plants. Lloydia, 33, 244–254.

Wichtl, M., Ed., 1994, Herbal Drugs and Phytopharmaceuticals, Trans. Bissett, N. G., CRC Press, Boca Raton.

Yang, Y. T. and McElligott, M. A., 1989, Multiple actions of beta-adrenergic agonists on skeletal muscle and adipose tissue. Biochem. J., 261, 1–10.

BACKGROUND ART

It has long been known that natural and synthetic substances may facilitate weight loss in those who are overweight or obese. Such substances as have found utility in this respect may act by a variety of mechanisms. For example, some such substances act by mimicking the effects of endogenous neurotransmitters, and are capable of directly replacing these neurotransmitters in their actions on receptors. This, in turn, leads to increased activity of the cells which possess the receptors. Where the receptors concerned are normally responsive to the endogenous hormones adrenaline (epinephrine) and noradrenaline (norepinephrine), which mediate the activities of the sympathetic nervous system, such substances are termed direct-acting sympathicomimetic agents. Typical examples are the amphetamines. Other substances that produce similar effects on the sympathetic nervous system do so by stimulating the release of the endogenous hormones adrenaline and noradrenaline, and are thus termed indirect-acting sympathicomimetic agents. Ephedrine is a typical example of an indirect-acting sympathicomimetic agent. The term adrenergic may also be used, and is synonymous with the term sympathicomimetic. Such substances may also be referred to as agonists, where the name agonist is qualified by a descriptor of the receptor stimulated, for example, a beta-agonist.

While the formal distinction between direct-acting and indirect-acting sympathicomimetic action is clear, it is realized that many substances which act by causing sympathetic stimulation do so by both mechanisms, depending on intake levels and the receptors involved. Thus amphetamines act mainly directly, but also have some indirect actions, while ephedrine acts indirectly, but if given in higher dosage, may also stimulate receptors directly, particularly in the brain. It has been demonstrated that the main perceived actions of sympathicomimetic agents depend both on their differing specificities for the various receptors and on the pharmacokinetic behaviors of the agents in the body.

Thus the amphetamines, which are direct agents and readily cross the blood-brain barrier, mainly cause central nervous system stimulation, while ephedrine, and particularly pseudoephedrine, are indirect agents which do not cross the blood-brain barrier so readily, and thus are mainly seen to exert peripheral effects.

Another class of substances of value in assisting weight loss modulates other neurotransmitters, namely those involved in serotoninergic systems, and particularly 5-hydroxytryptarnine (5-HT; otherwise known as serotonin) itself. These substances, of which fenfluramine and its optical isomer, dexfenfluramine, are typical, act by preventing the re-uptake of serotonin into storage granules in neurones. Levels of 5-HT in the synaptic gap thus remain elevated for longer periods, exciting receptors on responsive cells to greater activity.

Other aids to weight loss have been proposed, such as substances which prevent the absorption of nutrients from the digestive system, but the value of such approaches is minimal, and in general, the accepted substances of value in weight loss act by modulating neurotransmitter function in the central nervous system or peripherally.

Substances which modulate neurotransmitter function in the central nervous system are known to act by increasing the availability of catecholamines, in particular noradrenaline, in certain areas of the brain, thus resulting in perceived suppression of hunger. By suppressing hunger, less food is eaten, and caloric intake is lowered. Examples of such substances include phenylpropanolamine, phentermine and the amphetamines.

Substances which act by increasing the availability of 5-hydroxytryptamine (serotonin), on the other hand, are known to increase perceptions of satiety. An example of such a substance is dexfenfluramine.

Irrespective of mechanism, substances of either of these types result in reduced food intake. But their use can be attended by various unwanted effects characteristic of interference with other hormone-regulated systems in the body. It has furthermore been noted that the effects of these types of substances are transient, requiring progressively greater dosage to elicit desired effects, until the body finally becomes unresponsive. This progressive decrease in sensitivity is termed tachyphylaxis.

More recently, attention has been focused on ephedrine, which was originally thought to suppress the hunger center in the brain. However, during the last 30 years, research has shown that ephedrine acts mainly by stimulating thermogenesis. That is, it increases the metabolic rate and stimulates lipolysis (fat breakdown).

The effect of ephedrine on the peripheral metabolic rate is derived from actions on energy-generating tissues combined with stimulation of the release of fat from stored fat depots (adipose tissue). This not only increases the generation of energy but also increases the availability of substrates to be utilized for this energy generation. A valuable consequence of these two actions is the sparing of body protein, which in certain cases, depending on the composition of the diet, may even result in a gain of body protein (anabolic effect).

The effects of ephedrine can often be intensified by concomitant use of methylxanthines such as caffeine.

Empirical studies have shown that ephedrine, whether as the pure substance or in the an form of Ephedra herb:

(a) Improves rates of weight loss in patients on low calorie diets, spares lean body mass (Pasquali et al., 1992; Kaats and Adelman, 1994), increases the proportion of fat in the weight lost (Astrup et al., 1992b) and prevents the decline in Resting Metabolic Rate usually seen with reduced caloric intake (Astrup et al., 1992b; Astrup and Toubro, 1993).

(b) Gives results, through increased thermogenesis and stimulation of lipolysis (fat breakdown) at dosage levels below those required to elicit stimulant or hunger suppressant effects (Astrup and Toubro, 1993).

(c) Shows synergism in the effects on weight loss when combined with caffeine (Daly et al., 1993; Astrup and Toubro, 1993).

(d) Is not associated with significant adverse effects. Thermogenic effects became more pronounced as treatment continues (Astrup et al., 1985, 1986) while initial adrenergic effects (which are not pronounced) exhibit tachyphylaxis and rapidly disappear (Astrup et al., 1992a).

It has even been suggested that ephedrine may be an example of a trace substance that belongs in the human diet, and that it provides an opportunity to attack obesity at a level that is close to causative (Landsberg and Young, 1993).

Based on the clinical observations, ephedrine may therefore be considered an ideal pharmacological aid in the treatment of obesity.

Though it has some central stimulant effect, and thus mediates suppression of hunger, ephedrine's main mode of action appears to be peripheral and, in part, causative since it offsets the decline in metabolic rate that normally occurs on caloric restriction. The decline in metabolic rate that accompanies caloric restriction, therefore, is well known to those schooled in the art to defeat the initial weight loss benefits associated with caloric restriction. The body, in effect, recognizes the "starvation" period, becomes more efficient in utilizing caloric resources, and simply waits until normal caloric intake is resumed. This explains the "plateau" effect seen in caloric restriction diets. When normal caloric intake is resumed, the body's increased efficiency actually restores the fat lost in the caloric restriction period. This is a commonly known as the "yo-yo dieting" effect.

The thermogenic action which results from ephedrine's effects on metabolic rate and lipolysis persists throughout its use period, and may intensify as use continues.

Ephedrine's classical adrenergic actions, which are undesirable in a weight loss context, cease rapidly due to tachyphylaxis.

The classical uses of ephedrine and pseudoephedrine for a variety of conditions are well illustrated by reference to standard works on Pharmacology and Therapeutics. For example, Govoni and Hayes (1985) describe use of ephedrine as a decongestant in allergic rhinitis, sinusitis and chronic asthma (often combined for such indications with theophylline, a methylxanthine closely related to caffeine in structure and effect), in the treatment of narcolepsy, to combat hypotensive states (especially those associated with spinal anesthesia), in the management of enuresis, as adjunctive therapy for myasthenia gravis, as a mydriatic, as temporary support of ventricular rate in Adams-Stokes syndrome, to relieve dysmenorhoea, and for management of peripheral edema secondary to diabetic neuropathy. Streeten (1975) adds idiopathic edema to the list of conditions where ephedrine (150–200 mg per day) has beneficial activity, and other uses verified have included ketotic hypoglycaemia (Court et al., 1974), urological syndromes caused by prostaglandin El (Lowe and Jarow, 1993) and insulin-induced edema (Hopkins et al., 1993). Matthews (1983) discusses the action of ephedrine on the internal sphincter of the bladder and urethra in relation to its use in treating urinary incontinence. Govoni and Hayes (1985) note that maximum parenteral dosage should not exceed 150 mg/day by subcutaneous (s.c.), intramuscular (i.m.) or intravenous (i.v.) routes and comment that unwanted effects (all of which are consequent on the pharmacology involved) usually only occur with large doses. The same textbook teaches that pseudoephedrine essentially shares these properties, but is mainly used for relief of rhinitis in doses up to 240 mg/day for adults; Southon and Buckingham (1989) concur that pseudoephedrine and ephedrine have similar pharmacological profiles, but that pseudoephedrine is less potent.

Naturally occurring ephedrine is the 1R,2S(-)-erythro form, which is the most active pharmacologically. Pseudoephedrine is the threo form.

Acting indirectly, the main action of ephedrine is to elicit release of noradrenaline (norepinephrine) from presynaptic sites. This in turn activates both alpha- and beta-adrenoceptors. The perceived effects on different organs and tissues depend on the relative proportions of the two types of receptors, which mediate different responses. At a basal level, classical pharmacology teaches that alpha-activation results in contraction of smooth muscle (except for intestinal smooth muscle) while beta-activation causes relaxation of smooth muscle and stimulation of the myocardium. But this picture is complicated by the fact that both alpha- and beta-receptors can be subdivided into fuirther types with differing distributions and sensitivities.

At a cellular level, activation of beta-receptors results in stimulation of adenylate cyclase. This leads to increases in intracellular levels of cyclic adenosine monophosphate (cAMP). The precise sequence of events (Munson, 1995) is believed to be:

(1) The beta-agonist binds to the beta-receptor.

(2) The receptor-agonist complex has high affinity for a stimulatory guanine nucleotide regulatory protein termed the Gs protein, and binds to this protein.

(3) Formation of the receptor-agonist-Gs complex facilitates the exchange of a guanine diphosphate (GDP) for guanine triphosphate (GTP) on the Gs protein.

(4) The Gs-GTP complex dissociates from the receptor-agonist complex and then interacts with the catalytic subunit of adenylate cyclase, promoting the conversion of adenosine triphosphate to cAMP.

(5) The cAMP activates a cAMP-dependent protein kinase, which can then phosphorylate a variety of intracellular proteins, ultimately leading to a pharmacological response.

Feedback inhibition control is achieved by phosphorylation of receptor proteins, which results in their desensitization.

Activation of most alpha-2 receptors has an opposite effect, the first step being inhibition of adenylate cyclase through a guanine nucleotide regulatory protein termed Gi. The Gi protein, by inhibiting the catalytic activity of the adenylate cyclase, leads to a reduction in cellular levels of cAMP, which decreases the activation of the cAMP-dependent protein kinases. However, in some alpha-2 receptors, the Gi protein may act through other mechanisms which have not yet been elucidated, but possibly lead to activation of membrane calcium channels.

The alpha-1 receptors have a different mechanism. It does not appear to involve cAMP, but apparently relies instead on diacyl glycerols and inositol-1,4,5-triphosphate.

It is readily understood that the beta-receptors can also be further subdivided based upon their mechanism of action. The known subdivision of beta-receptors into beta-1, beta-2, and beta-3 types is of particular interest for this invention since the beta-3-receptor is strongly believed to be responsible for the lipolytic and thermogenic effects of ephedrine while interactions with the other two types of beta-receptors are known to control cardiac effects of ephedrine.

Effects on blood pressure, however, are in part due to the stimulation of alpha-2-receptors, where such stimulation produces peripheral vasoconstriction.

Central nervous system effects of ephedrine appear to depend on activation both alpha- and beta-receptors (with the exception of beta-3-receptors). The multi-receptor response to ephedrine is also important in explaining observed synergistic effects of caffeine on certain actions of ephedrine.

The overall response to ephedrine, reflected in perceived effects, is governed by the distribution of receptors in terms of types and populations. As an example, the activation of beta-receptors causes vasodilation of vessels in the heart and skeletal muscle while simultaneous alpha-2-activation results in vasoconstriction in other vascular beds. This is effectively the classical "fight or flight" response, which together with other metabolic results of adrenoceptor activation is intended to put the body into an optimal state for physical exertion.

The metabolic results of adrenoceptor activation also include effects on lipolysis and thermogenesis. In the case of lipolysis, activation of alpha-2-receptors inhibits the process, while activation of beta-receptors (believed to be the beta-3-subtype) stimulates lipolysis and at same time, possibly in part due to increased availability of substrate, induces a thermogenic response. The overall response of the adipose tissue thus depends on the relative proportions of alpha-2 and beta-3 receptors. A high ratio of alpha-2 to beta-3 receptors would produce a comparatively lower thermogenic response than a low ratio. Indeed, the predicted diminishment of thermogenic response associated with increasing proportion of alpha-2 compared to beta-3 receptors may explain why some studies of thermogenic responses to ephedrine have found two populations: responders and relative non-responders.

Attention has been paid to the unexpected finding that thermogenic properties of ephedrine do not exhibit tachyphylaxis. Landsberg and Young (1993) adopt the position that since the activity of the sympathetic nervous system may be reduced in obesity, improvement of sympathetic nervous system activity to normal levels is physiological rather than pharmacological, and that the use of ephedrine in obese persons does nothing more than restore normal catecholamine function. In this respect, therefore, ephedrine differs in no way from the effects of high protein diets or consumption of foods containing natural thermogenic substances. Lansdberg and Young also suggest that ephedrine may be particularly useful in combating the weight gain that usually follows cessation of smoking since smoking cessation is also associated with impaired catecholamine function.

Dulloo (1993) concurs with Lansdberg and Young's point of view. He notes that at levels compatible with therapeutic doses, ephedrine has little or no direct agonist activity but mediates its effects via endogenous release of noradrenaline and adrenaline. Essentially, therefore, ephedrine does nothing more than increase the efficiency of the system already in place in the body. He notes that this has potential positive implications for ephedrine's use in the treatment of obesity, and also explains some of the obscure clinical observations reported:

1) The fact that tolerance rapidly develops to the very mild cardiovascular effects of ephedrine, but not to its thermogenic effects, suggests that adrenaline and noradrenaline released by ephedrine activate the beta-3-adrenoceptors.

2) The adrenaline released is a preferential agonist for the beta-2-adrenoceptors which stimulate protein synthesis and thus can counteract loss of lean body mass during use of low calorie diets.

In this respect, Pasquali et al. (1992) have shown that ephedrine enhances fat loss in diet-restricted obese patients and reduces loss of nitrogen.

3) Chronic stimulation of postsynaptic alpha-adrenoceptors by the adrenaline and noradrenaline released in response to ephedrine therapy may activate thyroxine deiodinases, leading to peripheral conversion of T4 (thyroxine) to T3 (triiodothyronine), which may, in turn, increase adrenoceptor sensitivity to the thermogenic effects of the catecholamines since T3 is much more active than T4.

This mechanism may also partially explain why the thermogenic effect of ephedrine is increased after chronic administration.

4) Single dose studies have shown that skeletal muscle and visceral organs contribute most of the thermogenic activity after ephedrine administration, with a minor contribution from adipose tissue. These tissues can all be reactivated and even proliferate in response to chronic catecholamine activation, which may explain the enhanced thermogenesis seen with prolonged ephedrine treatment.

Dulloo suggests that ephedrine, with chronic administration, exerts its effects indirectly via adrenaline and noradrenaline and thereby generates its own selectivity for desirable anti-obesity effects. This is accomplished by the down-regulation of adrenoceptor types or subtypes associated with unwanted cardiac or pressor effects and with sustained activation of adrenoceptor types that mediate thermogenesis, lipolysis and protein retention.

Arner (1993) approaches the mechanism of ephedrine action from the lipolysis aspect. He notes that catecholamines have both lipolytic and antilipolytic effects, so that at any time there is a balance between these effects. However, it has been suggested that lipid metabolism in man is mainly controlled by inhibitory modulators, and adenosine has been shown to reduce the sensitivity of lipolytic beta-adrenoceptors, particularly in subcutaneous fat depots. Several prostaglandins of the E-type are also potent antilipolytic agents. Thus the potentiation of the ephedrine effect by caffeine (which may affect adenosine dynamics) and aspirin (which can inhibit prostaglandin synthysis) may not be restricted to the synaptic gap, but may also extend into the actual fat-mobilizing mechanism.

Dulloo (1993) noted that in early investigations of ephedrine use as an anti-obesity agent, attention focused on the main action of ephedrine in reducing appetite (the anorexic effect). It now appears that the thermogenic and lipolytic effects are the main properties that make ephedrine so suitable for use as a weight loss aid. Indeed, significant improvements of rates of weight loss occur at ephedrine dosage levels far below those required to achieve detectable main effects, and increasing dosage to the level at which main effects occur does not necessarily give better rates of weight loss (Daly et al., 1993).

While the actions of ephedrine makes it an ideal adjunct for regulating and controlling weight problems, it will be obvious to those skilled in the art that it may also be useful as an ergogenic aid to improve physical performance. The acute action is to increase energy availability and, thus, increase the capacity for physical exertion, while the longer-term actions result in an increase in muscle mass, particularly when combined with appropriate diet programs and training exercises. Indeed, Yang and McElligott (1989) have commented that beta-adrenergic agents may act as very effective anabolic agents when given over long periods of time. Both the beneficial ergogenic effects and the valuable effects on weight loss stem from the combination of the effects of ephedrine on lipolysis and its thermogenic effects. Thus by increasing the rate at which fat is released from body stores (lipolysis) while simultaneously increasing the metabolic rate (thermogenesis), those wishing to lose weight may accelerate the removal of unwanted fat stores.

At the same time, since the administration of ephedrine means there is increased availability of substrates (the free fatty acids which are released from the fat stores) for oxidation, the body has access to greater amounts of energy. The body's use of these substrates spares protein that might otherwise be oxidized for energy. Therefore, the use of ephedrine in conjunction with additional favorable circumstances, namely a high protein intake and an exercise program, will also result in increased availability of amino acids for incorporation into protein in the muscle mass.

From the foregoing, it will be obvious to those skilled in the art that the agents most suitable for inducing weight loss in those with excess weight, or, for persons of normal weight, increasing energy availability and/or muscle mass, would be sympathicomimetic (adrenergic) agents whose mechanism of action is mainly indirect, resembling that of ephedrine, and whose pharmacokinetics favor retention of the agents in the periphery rather than passage into the brain. Agents whose profiles match these requirements would be less likely to cause central nervous system stimulation under normal conditions of use, but would still possess enough central action to suppress the hunger center. The partition in favor of peripheral tissues would result in increased levels of these agents at the sites of the beta-3-receptors, which mediate lipolysis and thermogenesis. It is also widely believed that sympathicomimetic agents possessing mainly an indirect mechanism of action would be less likely to cause unwanted side effects and less likely to result in addictive situations.

Hitherto, the only such agent which has been shown to act in the optimized ideal fashion has been ephedrine itself. Ephedrine has some drawbacks, however. It is primarily provided in pharmaceutical forms which allow quick release in the body for the alleviation of acute respiratory ailments whereas, for the purposes of inducing lipolysis and thermnogenesis, a slower release is desirable. Furthermore, many of those who are overweight prefer not to use agents which are presented as drugs. In addition, for a variety of health conditions, such use will often be contraindicated because of the risk of potentially hazardous side effects, which risk could be increased because of the weight problem.

Prior to this invention, those wishing to avail themselves of natural products for eliciting weight loss or increasing muscle mass have had no choice other than to use products containing Ephedra herb (Ephedraceae), which contains ephedrine together with related alkaloids. However, because of concerns about the use of Ephedra herb products, many do not avail themselves of this opportunity.

The provision of a natural product that acts in the ideal fashion noted above would therefore provide major benefits to those seeking to lose weight or improve their physical fitness, or both, and would be especially useful to those who prefer not to take either drug-like products or natural products containing ephedrine alkaloids.

SUMMARY OF THE INVENTION

The present invention relates to the discovery that certain plants contain adrenergic amines of the group consisting of synephrine, hordenine, octopamine, tyramine and N-methyltyramine that are useful to assist in weight loss, adding muscle mass, and/or increasing physical performance. More particularly, the present invention relates to the discovery that useful and exploitable levels of these adrenergic amines only occur in plant species of Citrus.

In still greater detail, the invention relates to the discovery that these useful levels only occur in parts of the plant that are not normally eaten, including the leaves and bark, or in the fruit in certain stages of maturity. In yet further detail, the invention relates to a composition in which the plant parts are used in various forms to provide therapeutically effective doses of these adrenergic amines and to a composition in which the adrenergic amines are extracted from the plant parts using methods well known to those schooled in the art.

In further detail, the invention relates to the use of the composition to stimulate beta-receptors in a predominantly indirect fashion thereby stimulating thermogenesis, increased metabolic rate and lipolysis. In yet additional detail, the invention relates to the use of the composition to control appetite by suppressing hunger.

In further detail, the composition of the invention has utility in regulating or treating weight problems as well as increasing vitality, energizing, and in the long term increasing muscle mass.

In still further detail, the amounts of the adrenergic amines of this invention needed to be effective can be as low as one mg ingested three times daily, and the low dosage effective range is from one to five mg ingested up to 3 or 4 times daily. Still fuirther, the preferred use of this invention is to administer single doses of from 8 to 30 mg up to 4 times daily, making a total daily dose of about 100 to 120 mg per day.

In a further aspect, the present invention relates to a method for weight loss and a method for ergogenesis to aid in improved physical performance and to aid in adding lean muscle mass to the body.

An object of the present invention is to provide a composition containing an effective weight control/weight loss amount of at least one of the group of adrenergic amines synephrine, hordenine, octopamine, tyramine and N-methyltyramine.

Another object of the present invention is to provide a composition containing an effective amount of at least one of these adrenergic amines to stimulate the addition of lean muscle mass.

Yet another object of the present invention is to provide a composition containing an effective amount of at least one of these adrenergic amines to enhance physical performance.

Still another object of the invention is a method for promoting weight control, weight loss, enhanced physical performance, and/or the addition of lean muscle mass which includes the step of administering to a subject an effective amount of at least one of the group of five adrenergic amines.

Another object of the invention is to obtain the adrenergic amines from the plant material of the genus Citrus, and more specifically from the leaves, bark, unripe fruit, ripe fruit and peel of the species Citrus aurantium and/or Citrus reticulate.

In achieving the above and other objects, one feature of the invention is that the composition can be administered in the form of the plant material in a tablet, capsule or other pharmacologically appropriate carrier, in the form of a tea, or in the form without plant material in a tablet, capsule or other pharmacological carrier which contains at least one of the group of five adrenergic amines extracted from the plant material.

DETAILED EMBODIMENTS OF THE INVENTION INCLUDING BEST MODE

Figure 1:
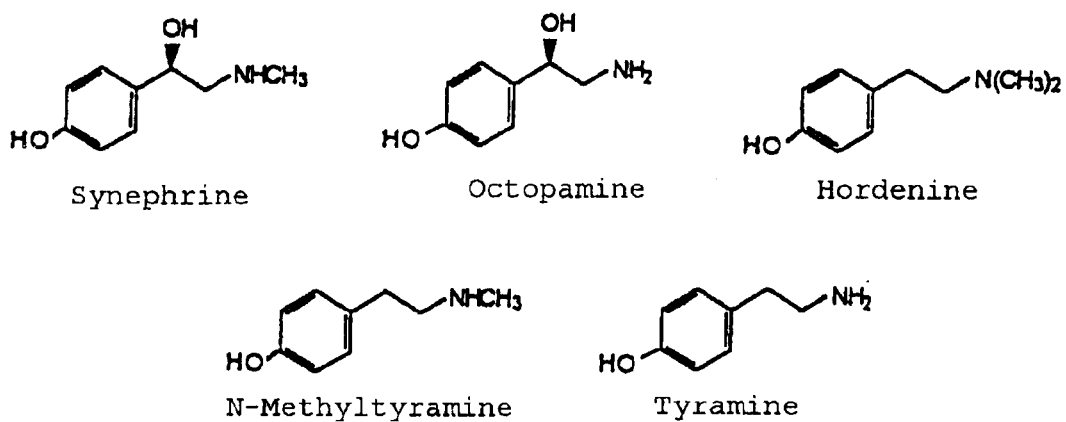
FIG. 1 shows the chemical structures of the five alkaloids: synephrine, hordenine, octopamine, tyramine and N-methyltyramine.

It has now surprisingly been found that agents present in plants other than Ephedraceae may also act as sympathicomimetic agents with suitable mechanisms of action in the body, and use of these plants can therefore result in benefits as outlined with regard to body weight regulation and physical performance.

The value of the use of such plants in body weight regulation and physical performance has not been suspected prior to this invention. Though the plants concerned have acknowledged uses and long histories as foods, they have not been used to induce weight loss or for ergogenic purposes. The agents these plants contain have likewise not previously been related to weight loss or ergogenic applications. Furthermore, the agents are generally only present in significant amounts in parts of the plant which are considered as inedible waste for normal consumption, or are only present during certain stages of the growth cycle when the plant would not normally be consumed. While it is true that the plants or their parts harvested during a particular stage of growth have also been used as medicinal herbs or traditional remedies, particularly in the Orient, these uses have also not included applications in either weight loss or for ergogenic purposes, and the uses according to the invention are therefore novel and surprising.

The agents contained in the plants which are used in accordance with the invention include synephrine, hordenine, octopamine, tyramine and N-methyltyramine, and they may be found in various species of plants, both food plants and otherwise, as detailed by Wheaton and Stewart (1970), including, but not limited to, Amaryllidaceae, Leguminosae, Liliaceae, Rutaceae, Cyperaceae, Solanaceae and Berberidaceae. FIG. 1 shows the chemical structures of synephrine, hordenine, octopamine, tyramine and N-methyltyramine.

However, in terms of practical utility, the levels of these agents generally only reach useful values, that is to say levels in excess of 0.1% of dry mass, in certain species of Rutaceae. Furthermore, these useful levels are only achieved during phases of growth where the plant would not normally be used for food, or in parts of the plant which are not considered part of the edible portion such as the leaves. In particular, relatively high levels of synephrine and related substances (such as octopamine, hordenine, tyramine and N-methyltyramine) can be found in various Citrus species, including in particular, but not restricted to, strains of Citrus reticulata (also known as tangerine or mandarin orange), *Citrus aurantium* (also known as *C. florida, C. vulgaris, C. bigaradia*, Sour orange, Bitter orange, Seville orange, Neroli orange), *Citrus medica, Citrus maxima, Citrus limon, Citrus aurantiifolia, Citrus paradisi, Citrus sinensis* and *Poncirus trifoliate* (trifoliate orange).

These various Citrus species have been used, and continue to be used, for a variety of food purposes and for their health benefits, but have hitherto not been revealed as herbs or plants which have value in the treatment of weight problems or for improving physical performance and fitness.

Herbs based on Citrus materials have long been used for a variety of medicinal applications unrelated to weight loss. In this respect, for example, the literature discloses a number of Oriental herbs for medicinal applications, including the following:

Zhi shi: The immature (dried) fruit of *Citrus aurantium* is used for the treatment of digestive disorders, to induce diuresis, and as a mucolytic agent to relieve chest congestion (Ou Ming, 1989). It may contain levels of the desired active agents of up to 0.9%. Reid (1986) describes Zhi shi as the unripe fruit of the trifoliate orange, indicated for digestive disorders and as an expectorant, while Huang (1993) implies that this herb is derived from mature fruits of *Citrus aurantium*.

Zhi Qiao: This herb is also the immature fruit of *Citrus aurantium*, and is used to treat indigestion and to correct mild ptosis of the uterus (Huang, 1993). Levels of active substances are similar to those in the herb Zhi shi, and the distinction between these two herbs appears to be based on degree of maturity (of the fruit) and the area in which traditionally used.

Chen pi: The herb Chen pi is dried peel of *Citrus reticulata*. This may also be called Jiu Hong, and is used as a digestive aid, antiemetic, antitussive and antiflatulant (Huang, op. cit.). The herb also has anti-infective properties (Ou Ming, op. cit.).

Qing pi: This herb is immature *Citrus reticulata*, or in some cases the peel thereof. It is used to treat digestive disturbances and to alleviate pain, as an expectorant, and to relax smooth muscle (Ou Ming, op. cit.).

Fo Shou: Also known as Fructus Citri Sarcodactyli, the fruit of *Citrus medica* var. sarcodactylus, it is used for treatment of digestive disorders, for dysmenorrhea, chest congestion and as an expectorant (Ou Ming, op. cit.).

According to Bown (1995), *Citrus aurantium* and *Citrus reticulata* are known by different Chinese names in part according to their uses. For example, the whole fruit, peel, unripe fruit, unripe peel and seeds of *C. reticulata* are referred to as "Chen pi" ("dried ripe peel") to treat indigestion, flatulence, vomiting and wet coughs, but as "Qing pi" ("unripe peel") when used to treat liver and gall bladder disorders, bronchial congestion, mastitis, breast cancer, and pain in liver, chest or breasts, while the form "Ju he" (Jiu hong; normally the seeds) is used to treat lumbago, orchitis and mastitis.

In Western traditional medicine, Wichtl (1994) describes use of the mature or immature fruit of *Citrus limon* for the treatment of digestive problems and phlebitis, and notes that the flowers of *Citrus aurantium* and occasionally *Citrus sinensis* are also used for their sedative effects. Wichtl also reports that dried peel of *Citrus aurantium*, or the dried whole immature fruit, is used in gastrointestinal remedies, tonics, roborants and cholagogues. Grieve (1992) describes use of lemon juice for the treatment of rheumatism, and of the oils from various oranges for alleviation of chronic bronchitis. Font Quer (1982) refers to the antispasmodic and hypnotic properties of *Citrus aurantium* flowers, and to the use of the dried peel as a gastric tonic and antiflatulant.

Numerous other standard textbooks of herbology refer to Citrus material of various types and its use for the alleviation of gastric disorders. However, neither the use of such materials to induce weight loss nor their use to increase physical performance or muscle mass are described, and these uses are therefore surprising, novel and not anticipated.

The active agents synephrine, hordenine, octopamine, tyramine and N-methyltyramine are known to be adrenergic agents, and synephrine is still used under the synonym oxedrine in some countries for the treatment of hypotension (Reynolds, 1982). However, apart from occasional use of tyramine as a diagnostic agent in suspected cases of phaeochromocytoma, their use has been abandoned in favor of newer, synthetic adrenergic agents, and no indication of their value in weight loss or physical performance can be found in the literature. Their valuable properties in these respects are therefore unanticipated, surprising and novel.

The Citrus material used in accordance with the invention may consist of any portion of the plant which contains useful amounts of the agents as defined above, which may vary depending on the species, stage of growth, season, and agronomic conditions. For example, leaves of *Citrus reticulata* are preferred to other parts of this plant, and may show levels of synephrine and related alkaloids of 1.1% or more, based on dry matter, while the peel of the immature fruit shows levels of only 0.2%–0.4%. In the case of *Citrus aurantium*, the preferred form is the whole immature fruit of the amara variety, though the peel of the mature fruit can also be used. In both *Citrus aurantium* cases, total levels of 0.2%–0.9% of synephrine and the related agents are regularly found. Both the peel and the whole fruit (immature or mature) of the dolce variety also have utility, though levels generally do not exceed 0.4%.

Though it is possible to use a variety of Citrus materials in accordance with the invention, it is more convenient to utilize Citrus materials which already exist in appropriate form and which are generally available as traditional herbs and remedies. For example, the agents are present in the residues remaining after steam distillation of *Citrus aurantium* fruits to obtain the essential oils. In this respect, various Chinese herbs, or materials from other geographic locations prepared in the same way, are particularly useful, as are *Citrus reticulata* leaves.

The Chinese herbs which are most convenient for use are:

Zhi shi, which is the immature (dried) fruit of *Citrus aurantium*, but may also consist of the peel of the mature fruit, or the peel of either. This herb contains 0.2%–0.9% total alkaloids with synephrine predominating.

Zhi Qiao, which is also the immature fruit of *Citrus aurantium* has levels of active substances similar to those in the herb Zhi shi.

Chen pi, the dried peel of *Citrus reticulate*, may also be called Jiu Hong. This herb contains 0.1%–0.4% total alkaloids.

Qing pi is the dried immature *Citrus reticulata*, or in some cases the peel thereof. This herb contains 0.1%–0.4% total alkaloids.

Fo Shou, also known as Fructus Citri Sarcodactyli, is the fruit of *Citrus medica* var. sarcodactylus. This herb contains 0.1%–0.3% total alkaloids.

In addition to the above, peel of the mature or immature fruit of *Citrus limon* may conveniently be obtained, since it is also an item of commerce, while tangerine leaves are also readily obtained at certain seasons.

In a preferred embodiment of the invention, therefore, material from Citrus species is given to humans by the oral route, either concurrently with caloric restriction or in the absence of caloric restriction, for the purpose of controlling body weight. The invention works predominantly by increasing thermogenesis, that is, by increasing the metabolic rate and facilitating lipolysis. The invention also exhibits a hunger-suppressing effect which may become more obvious in higher doses as well as in individuals in which the active agents pass the blood-brain barrier more readily. Thus, most users will benefit mainly from the thermogenic effect and additionally may also experience mild suppression of hunger such that both mechanisms operate simultaneously, thereby providing an added benefit. In addition, the said material can be given to humans, either with or without a high protein diet (>1.25 gm protein/kg ideal body weight/day), for the purpose of increasing physical performance in the short-term and to increase muscle mass and functionality in the long term.

The Citrus material so used is selected for its content of active agents as defined above such that the total amount of Citrus material ingested provides a sufficient amount of the active agents to achieve the desired effects. In this respect, the preferred embodiment consisting of a sufficient amount would be defined as at least 0.04 mg of active agents per kilogram ideal body weight per dose at any one time. In practical terms this corresponds to 2.8 mg for a person of 70 kg ideal body weight.

Ingestion of active agents in the range of 0.01 mg to 0.10 mg per kilogram of ideal body weight per serving will be effective in accomplishing the desired goal of weight loss, though more preferred is a range of 0.02 mg to 0.06 mg per kilogram of ideal body weight, and most preferred is 0.05 mg per kilogram of ideal body weight. Though ingestion of larger amounts of the agents will not diminish the beneficial effects, the effects may not necessarily be increased while the possibility of side-effects due to activation of other adrenergic systems would be increased. Thus, at an intake level of 1 mg per kilogram of ideal body weight per serving, it is possible that the adrenergic receptors in the cardiovascular and central nervous system could be activated thereby resulting in increases in blood pressure as well as tachycardia, nervousness, agitation, tremors, and insomnia.

Daily intake of the active agents for effective body weight loss according to the invention is in the range of 0.16 mg to 1 mg per kilogram of ideal body weight. Thus, an adult male whose desired body weight is 176 pounds would lose weight according to this.invention with servings of 4 mg, with total daily intake in the amount of 32 mg.

In this context, the active agents are deemed to be any one or more of synephrine, hordenine, octopamine, tyramine and N-methyltyramine, whereby the sufficient amount may be any one singly, or a combination of the agents that together provide a sufficient amount.

Because levels of the said agents are often relatively low and variable, and also because in their natural state the agents are associated with parts of the plant that are unpalatable, it may be difficult to achieve an intake of Citrus material in a volume sufficient to provide a suitable amount of the agents as defined above.

To enhance edibility, the Citrus material may be consumed as a concentrate or as an extract in either dry or liquid form. By producing a concentrate or extract, the levels of the agents in the material are increased to an effective level. There are several ways readily known to those schooled in the art which permit production of a concentrate or extract. The Citrus material may be enriched in the agents, for example, by extraction of the Citrus material with water, dilute acids or certain organic solvents, including mixtures thereof with water, followed by drying on a carrier of unconcentrated Citrus material, or by drying on a carrier of another suitable material. Such a suitable material may include, but is not limited to, maltodextrins, starch, protein or other carrier material, the nature of which will be obvious to those skilled in the art of manufacturing extracts of botanical materials. The Citrus material may also be extracted and concentrated without drying to give a liquid extract that can also be consumed.

When prepared as an extract or concentrate, the Citrus material is preferably dried so that it may be given in the form of tablets, capsules, powders or other convenient form, or it may be admixed with foods or special food products, or it may be given in the form of a tea or tisane. When prepared as a liquid extract, the Citrus material may be consumed as drops, or from an appropriate liquid measure (teaspoon), or it may be admixed with other liquids or incorporated into solid food products. Preparation as an extract or concentrate permits production of standardized amounts of the active agents so as to produce a less variable response in terms of desired weight loss and/or the desired increase in muscle mass.

If it is not prepared as an extract or concentrate, the Citrus material may be given fresh, but is preferably dried so that it may be given in the form of tablets, capsules, powders or other convenient form, or it may be admixed with foods or special food products, or it may be given in the form of a tea or tisane.

For example, the dried leaves of *Citrus reticulata* var. Blanco may be filled into tea bags to give a refreshing vitalizing drink that enervates and suppresses hunger for long periods, while dried immature fruits of *Citrus aurantium* var. amara are best milled to a fine powder and either tabletted or filled into capsules for repeated oral administration to achieve similar effects over a period of weeks or months.

The Citrus materials may also be admixed with other ingredients to form the basis of a dietary product, which may either be a nutritional drink or a nutritional bar. One such nutritional bar can provide 15 grams of protein, 26 grams of carbohydrate and 5 grams of fat in addition to a quantity of the Citrus material. Such products may thus be used as meal replacements by those seeking to lose weight, or by those requiring nutritional support during sporting activities, whereby the benefits of the Citrus material are supported by the nutritional content of the food product.

The Citrus material, either in the form of an extract or as the natural material, may also be given in combination with other herbs that possess beneficial effects for humans, and particularly in respect to weight loss or improvements in physical performance. In this connection, suitable herbs and foods include those herbs and foods that contain methylxanthines such as caffeine, theobromine and theophylline, which by virtue of their inhibition of the enzyme phosphodiesterase may potentiate the thermogenic actions of the Citrus materials and increase the actions at the level of the beta-3-receptors. At the same time, the actions of methylxanthines on alpha-receptors may serve to reduce or eliminate any unwanted cardiovascular effects, such as peripheral vasoconstriction and increase in blood pressure, that would be undesirable within the context of weight loss or improved physical performance. Suitable herbs and foods in this respect include, but are not limited to, *Paullinia cupana* (Guarana), Ilex paraguariensis (Maté), *Cola nitida, Cola acuminata, Camellia sinensis* (Tea), *Coffea arabica* (Coffee) and *Theobroma cacao* (Cocoa), whereby the herb or food may be used as the natural material or an extract thereof In such cases, the herb so chosen is admixed with the Citrus material in a suitable form to provide a solid or liquid dosage unit.

The invention is further exemplified and illustrated by the following examples which are not limiting.

EXAMPLE 1

Tea-bags containing each 2.5 grams dried tangerine leaves (*Citrus reticulata* var. Blanco) were prepared. The tangerine leaves had a synephrine content of 1.1% and approximately 0.5% of the related alkaloids, which did not resolve completely on HPLC analysis, thus providing a total amount of 40 mg of alkaloids per serving. The tea bags were infused for 5 minutes in hot water at 85° C., and the resulting tisane was given to 5 volunteers (GL, RE, NS, CS, PS). All volunteers reported increased energy, which in one case was perceptible as agitation and nervousness, persisting for 8–10 hours. During this period, subjects did not feel hungry and refrained from eating snacks or meals.

EXAMPLE 2

A Zhi shi powder (*Citrus aurantium*, var. amara, whole immature fruit dried) was obtained from a Chinese source. This powder contained 0.49% synephrine and approximately 0.5% of the related alkaloids. It was mixed with 2% magnesium stearate and 1% silicon dioxide to confer flowability and filled into white size 0 snap-fit capsules. Capsule fill weight was 490 mg, plus or minus 5%. Subjects DJ and HAF then took 3 capsules 3 times daily for four weeks, corresponding to an intake of 14 mg total alkaloids per serving, or 42 mg per day, without deliberate restriction of food intake. Subject DJ, initial weight 105.4 kg, showed a fall in body weight to 100.9 kg, while the body weight decrease in subject HAF was from 74.5 kg to 72.0 kg. Upon ceasing use of capsules, subjects showed slow increases in body weight at a rate of approximately 0.4 kg per week.

EXAMPLE 3

A portion of the Zhi shi powder used in Example 2 was concentrated by extraction with water and redrying on a portion of the original material to give a dry extract with a total alkaloid content of 3.77%, of which approximately 1.9% was synephrine itself. This material was filled into capsules as in Example 2 to provide a product with 18 mg alkaloids of the synephrine group per capsule. Subjects DJ and HAF then took 1 capsule of this product 3 times daily for four weeks, providing a daily intake of 54 mg synephrine and related alkaloids. During this time, subject DJ, without deliberate restriction of food intake, showed a decrease in weight from 93.2 kg to 90.4 kg, but subject HAF had to cease use after the first day because of unpleasant sensations of agitation and nervousness.

EXAMPLE 4

Two batches of nutrition bars were prepared using the Thermobar concept, that is, chocolate-flavored taffy bars weighing 57 grams providing 15 grams protein, 26 grams carbohydrate, 5 grams fat and 200 kilocalories. One batch of the bars additionally contained 0.5 grams of the extract from Example 3 per bar. Subject RE was given two of the placebo bars. Respired gases were collected by the Douglas bag technique starting 30 minutes before ingestion of the bars and for a 90 minute period thereafter. The respiratory quotient (RQ) was initially 0.78 and rose to 0.86 during the 60 minutes after bar consumption. Two days later following the identical protocol, the subject consumed two of the bars containing the Zhi shi extract, corresponding to about 38 mg of synephrine and related alkaloids; respiratory quotient rose from 0.77 to 0.89 during the 60 minutes after bar consumption. Conversion of these results of indirect calorimetry to energy expenditure showed that the Zhi shi extract had increased the energy expenditure and the thermic response to the food by about 2.5%, thus indicating a thermogenic effect of the ingested alkaloids.

EXAMPLE 5

A group of 9 women, of whom 6 were mildly obese, 1 moderately obese and 2 slightly overweight, with Body Mass Indices ranging from 23.1 to 33.4 were placed on a diet providing 900–1000 kilocalories per day, more than 100 g protein per day and less than 100 g carbohydrate per day. From day 8 of this dietary regime, they were additionally given a product in capsules identified as "Herbal Balance Z-4", providing each 325 mg of a dried *Citrus aurantium* (immature whole fruit) extract, 125 mg of a dried Paullinia cupana extract, 5 mg of Ginkgo biloba extract and 5 mg Panax ginseng extract. They were instructed to take 1–3 capsules 1–3 times per day, and to remain at a comfortable intake level within these parameters; 2 subjects stabilized at 2 capsules per day, 2 at 3 capsules per day, 2 at 4 capsules per day and 3 at 5 capsules per day. The *Citrus aurantium* extract contained 4.14% total alkaloids by HPLC, with approximately 2.8% as synephrine itself. The daily use recorded thus corresponds to a total alkaloid intake of 27.0 to 67.5 mg.

Starting weights, weights at day 8, and weights at day 15 were determined. In addition, each subject completed a daily mood, appetite and satiety rating questionnaire.

| Subject | Age: | Height (m) | BMI: | Weights (kg): Day 0 | Day 8 | Day 15 |
|---|---|---|---|---|---|---|
| HS | 38 | 1.57 | 24.9 | 61.4 | 60.5 | 57.3 |
| GA | 40 | 1.67 | 29.7 | 82.7 | 81.6 | 80.0 |
| CB | 25 | 1.65 | 23.1 | 62.7 | 62.7 | 60.0 |
| CA | 46 | 1.61 | 26.7 | 69.1 | 68.2 | 64.5 |
| LG | 30 | 1.60 | 25.7 | 65.8 | 64.5 | 62.8 |
| AW | 41 | 1.64 | 33.4 | 90.1 | 88.6 | 85.4 |
| AEM | 31 | 1.67 | 23.8 | 66.6 | 65.4 | 64.1 |
| CRT | 23 | 1.73 | 25.9 | 77.5 | 76.8 | 74.5 |
| LB | 29 | 1.62 | 26.0 | 68.2 | 67.3 | 65.4 |

A statistical analysis showed a mean of 0.94 kg during the first week when no product was given and 2.40 kg during the second week when product was taken, the Z-4 product significantly increased weight loss (P<0.05) during the second week.

STATISTICAL ANALYSIS

Means ± standard deviations:

| | Body Weight (kg) | Weight Loss (kg): |
|---|---|---|
| Day 0 | 71.57 ± 9.75 | |
| Day 8 | 70.62 ± 9.54 | 0.94 ± 0.43 |
| Day 15 | 68.22 ± 9.54 | 2.40 ± 0.84 |

Full data on body weight indicated:

| Day: | Mean: | SD: | Median: | Minimum: | Maximum: |
|---|---|---|---|---|---|
| 0 | 71.57 | 9.75 | 68.20 | 61.40 | 90.10 |
| 8 | 70.62 | 9.54 | 67.30 | 60.50 | 88.60 |
| 15 | 68.22 | 9.54 | 64.50 | 57.30 | 85.40 |

Full data on weight loss indicated:

| Day: | Mean: | SD: | Median: | Minimum: | Maximum: |
|---|---|---|---|---|---|
| 8 | 0.94 | 0.43 | 0.90 | 0.00 | 1.50 |
| 14 | 2.40 | 0.84 | 2.30 | 1.30 | 3.70 |

This result is particularly interesting, since part of the observed weight loss during the first week was due to water loss as a result of changes in electrolyte and water balance (adaptation to reduced caloric intake).

The foregoing description represents the best mode presently known to the inventor of practicing the invention, and is not intended to limit the scope of the present invention which is set forth in the following claims. Likewise, those skilled in the art, given the present disclosure, will recognize that equivalent methods and materials may also be used in practicing the invention. It is contemplated that such equivalents are also within the scope of the present invention.

What is claimed is:

1. A method for stimulating thermogenesis in humans by administering by mouth to a subject a composition containing at least one of the substances selected from the group consisting of synephrine, hordenine, octopamine, tyramine and N-methyltyramine in therapeutically effective amounts.

2. The method according to claim 1 wherein the composition is a plant material containing at least one of said substances.

3. The method according to claim 2 wherein the amount of the substances is about three to four percent by weight which is effective to increase the metabolic rate of the subject without inducing increased caloric intake.

4. The method according to claim 1 wherein the dosage is at least 0.02 mg per kg of ideal weight which is effective to increase the metabolic rate of the subject without inducing increased caloric intake.

5. A method for reducing the weight of a human, which comprises administering to the human a thermogenically effective dose of a plant material containing at least one of the substances selected from the group consisting of synephrine, hordenine, octopamine, tyramine and N-methyltyramine.

6. A method for reducing the adipose tissue mass/lean mass body mass ratio of a human, which comprises administering to the human a thermogenically effective dose of a plant material containing at least one of the substances selected from the group consisting of synephrine, hordenine, octopamine, tyramine and N-methyltyramine.

7. The method according to claim 2, wherein said plant material is a citrus material.

8. The method according to claim 7, wherein said citrus material is obtained from a species selected from the group consisting of *Citrus reticulata, Citrus aurantium, Citrus medica, Citrus maxima, Citrus limon, Citrus aurantiufolia, Citrusparadisi, Citrus sinensis* and *Poncirus trifoliate*.

9. The method according to claim 5, wherein said plant material is a citrus material.

10. The method according to claim 9, wherein said citrus material is obtained from a species selected from the group consisting of *Citrus reticulata, Citrus aurantium, Citrus medica, Citrus maxima, Citrus limon, Citrus aurantiifolia, Citrusparadisi, Citrus sinensis* and *Poncirus trifoliate*.

11. The method according to claim 6, wherein said plant material is a citrus material.

12. The method according to claim 11, wherein said citrus material is obtained from a species selected from the group consisting of *Citrus reticulata, Citrus aurantium, Citrus medica, Citrus maxima, Citrus limon, Citrus aurantuifolia, Citrusparadisi, Citrus sinensis* and *Poncirus trifoliate*.

\* \* \* \* \*